United States Patent [19]  [11] Patent Number: 4,851,539
Johnston et al.  [45] Date of Patent: Jul. 25, 1989

[54] 2,3-DIFLUOROPYRIDINE AND 3-FLUORO-2-PYRIDINYLOXYPHENOL COMPOUNDS

[75] Inventors: Howard Johnston, Walnut Creek; Lillian H. Troxell, Antioch, both of Calif.

[73] Assignee: The Dow Chemical Company, Midland, Mich.

[21] Appl. No.: 799,702

[22] Filed: Nov. 19, 1985

Related U.S. Application Data

[60] Division of Ser. No. 497,295, May 23, 1983, Pat. No. 4,565,568, which is a continuation-in-part of Ser. No. 389,840, Jun. 18, 1982, abandoned.

[51] Int. Cl.$^4$ ............... C07D 213/26; C07D 213/64
[52] U.S. Cl. .................. 546/345; 546/301; 546/302
[58] Field of Search ............ 546/345, 301, 302

[56] References Cited

U.S. PATENT DOCUMENTS 4,302,242 11/1981 Cartwright .................. 71/94
4,508,907 4/1985 Cartwright .................. 546/345

FOREIGN PATENT DOCUMENTS 1599121 9/1981 United Kingdom .................. 71/94

*Primary Examiner*—Alan L. Rotman
*Attorney, Agent, or Firm*—Craig E. Mixan; Ronald G. Brookens

[57] ABSTRACT

Certain novel pyridinyloxyphenoxy alkanoic acids, pyridinylthiophenoxy alkanoic acids, derivatives thereof and related compounds are described. More specifically, these novel compounds bear a fluorine substituent in the 3-position of the pyridinyl group and in the 5-position the substituent is selected from chlorine, $CF_3$, $CF_2Cl$ or $CF_2H$. These novel compounds exhibit surprising preemergent and postemergent activity in the control of grassy weeds.

3 Claims, No Drawings

2,3-DIFLUOROPYRIDINE AND 3-FLUORO-2-PYRIDINYLOXYPHENOL COMPOUNDS

CROSS-REFERENCE TO RELATED APPLICATION

This is a divisional of application Ser. No. 497,295, filed May 23, 1983, U.S. Pat. No. 4,565,568, which is a continuation-in-part of application Ser. No. 389,840, filed June 18, 1982, abandoned.

BACKGROUND OF THE INVENTION

1. Field of the Invention

This invention relates (a) to novel pyridyl(oxy/thio)-phenoxy compounds, (b) to herbicidal compositions of such novel compounds and (c) to methods of using such compounds for the preemergent and postemergent control of grassy weeds in non-crop areas as well as in the presence of certain valuable crops such as soybeans, cotton and wheat.

2. Description of the Prior Art

Belgian Pat. No. 834,495, issued Feb. 2, 1976, as well as the published German patent application equivalent thereto, viz., No.2,546,251, published Apr. 29, 1976, describe 2-((4-pyridinyl-2-oxy)phenoxy)alkanoic acids, salts and esters having halo substitution in the 3- and/or 5-ring positions in the pyridine ring. Later references, e.g. published British Patent application 2,026,865 disclose such compounds having trifluoromethyl substitution on the pyridine ring and European Pat. No. 0002800 describes the enhanced effect of the D-stereoisomers of such compounds.

SUMMARY OF THE INVENTION

The present invention is directed to novel pyridyl(oxy/thio)phenoxy compounds having herbicidal activity and which correspond to the formula

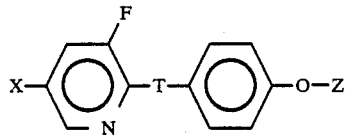

wherein X is $CF_3$, $CHF_2$, $CClF_2$, Br or Cl; T is O or S; and Z is an organic moiety containing N, O or S atoms or a metallic, ammonium or organic amine cation and is or can be hydrolyzed and/or oxidized in plants or soil to a carboxyl moiety that is in undissociated and/or dissociated form. The invention is also directed to the novel stereoisomers of such compounds, the R-isomers having exceptional activity.

A variety of herbicidal compounds containing substituted pyridyl and phenoxy moieties joined via a bivalent —O— and —S— are described in the art. For example, U.S. Pat. Nos. 4,046,553; 4,317,913; 4,267,336; 4,213,774; 4,324,627 and 4,309,547 and U.S. Patent application Ser Nos. 262,063 and 261,109, both filed July 30, 1980; Ser. No. 817,943, filed July 22, 1977 and Ser. No. 918,550, filed June 23, 1978, all describe such compounds, methods of making them, compositions containing them and methods of utilizing said compositions. These teachings are incorporated herein by reference. In general, the moieties bonded to the pendant —O— group of the phenoxy in the herbicidal compounds described in these references will also be suitable as the monovalent organic radical represented by Z in the formula for the aforementioned novel compounds and, given the appropriate pyridine starting material, the compounds of this invention can be prepared by methods described in the above-mentioned prior art, and can be utilized in compositions as described in said prior art.

Z moieties include, but are not limited to

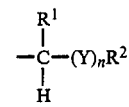

wherein Y is a saturated or unsaturated alkyl group containing an even number of carbon atoms, preferably from 2 to 18 carbon atoms, n is 0 or 1, $R^1$ is H or a $C_1$-$C_3$ group and $R^2$ is selected from moieties corresponding to one of the following formulae:

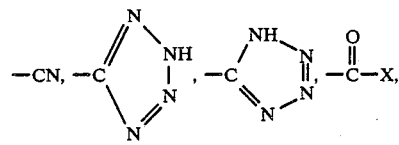

wherein X is halogen, or Cn,

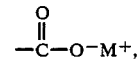

wherein M is a metallic cation, ammonium or an organic amine cation typically, but not exclusively, containing alkyl (saturated or unsaturated), alicyclic, heterocyclic or aromatic groups, all unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl,

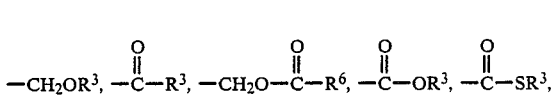

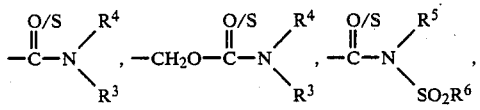

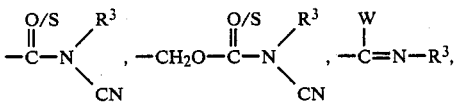

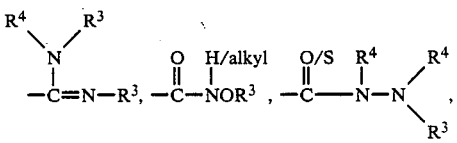

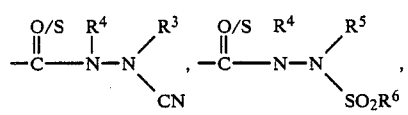

-continued

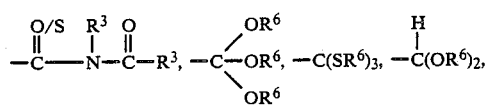

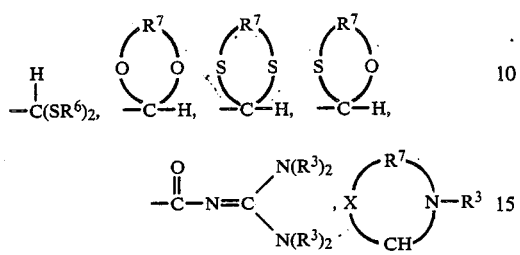

where X is S or O, where W is halogen; $R^3$ is H or $R^6$; $R^4$ is H, alkoxy or $R^6$; $R^5$ is H, a metallic cation or $R^6$; and $R^6$ is an alkyl (saturated or unsaturated), alicyclic, heterocyclic or aromatic group, unsubstituted or substituted with various other groups not limited to, but including, halo, cyano, nitro and unsubstituted or substituted thiol, hydroxy, amino or carboxyl groups and, additionally, alicyclic, heterocyclic and aromatic groups substituted with unsubstituted or substituted saturated or unsaturated alkyl groups, for example, trifluoromethyl, chloromethyl, cyanomethyl and vinyl,

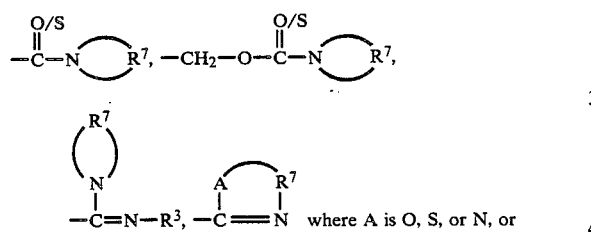

where $R^7$ completes an unsubstituted or substituted saturated heterocyclic ring system.

The above derivatives can be made by processes generally known to those skilled in the art and as described in the above-mentioned patents. For example, the corresponding acid chlorides can be reacted with a Grignard reagent to make the desired aldehyde or ketone derivative. Similarly, reaction of an acid chloride with KSH will provide the desired thiol acid. Thioamides may be prepared from the corresponding amide by reaction with $P_2S_5$ or, if hydrogen is present on the nitrogen atom, the carbonyl may be converted to, e.g., chloride, with removal of HCl, followed by reaction with hydrogen sulfide. Carbamoyl chlorides are available in the art or they may be prepared from the desired amine and phosgene and thiophosgene for use in making compounds containing the

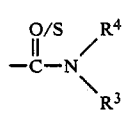

ps group.

The reaction of an amine with a sulfonyl chloride, e.g., $R^5NH_2 + R^6SO_2Cl$ provides the group

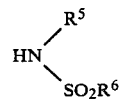

for use in reacting with an appropriate acid chloride.
The reaction of an amine with BrCN provides,

which reacts with the appropriate acid chloride to provide compounds containing the

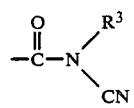

moiety. $P_2S_5$ is employed to make the corresponding S-containing compound.

Reaction of the above cyanoamine with phosgene or thiophosgene provides

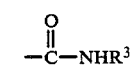

for use in making the corresponding derivatives.
The reaction of the compounds having the moiety

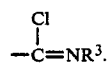

with $PCl_5$ will provide compounds having the moiety

The reaction of the corresponding acid chloride with $RONH_2$ will provide compounds having the group $$-\overset{O}{\overset{\|}{C}}-\overset{H}{\overset{|}{N}}-OR.$$

Various hydrazine derivatives can be made, e.g., from trimethyl hydrazine by reaction with the acid chlorides. The reaction of the amides, e.g.,

with dicarboxylic anhydrides will provide compounds having the group

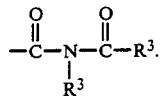

$R^2$ is preferably a carboxylic acid group, an alkali or alkaline earth metal salt thereof, an ammonium or organic amine salt thereof or a lower alkyl ester thereof, wherein "lower alkyl" includes straight, branched or cyclic saturated or unsaturated alkyl groups containing no more than 6 carbon atoms. Preferably, n is 0.

In the above formulae the aliphatic groups preferably contain 1 to 6 carbon atoms, the alkenyl and aklynyl groups preferably contain 2 to 6 carbon atoms, the alicyclic groups preferably contain 3 to 6 carbon atoms and the aromatic moiety is preferably phenyl, although other ring systems, including heterocyclic ring systems, may be employed if desired.

In the formula for the aforementioned novel compounds, T is preferably O and X is preferably $CF_3$, Cl or Br. Most preferred are the compounds in which X is $CF_3$ or Cl, T is O, and Z is

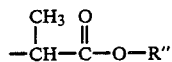

wherein R'' is methyl, ethyl, propyl, isopropyl, isobutyl or n-butyl.

The compounds of the above formula, hereinafter referred to for convenience as "active ingredients", have been found to be especially active as herbicides for the control of undesired vegetation, for example, grassy or graminaceous weeds and are unexpectedly more effective than the compounds of the known art. Especially surprising is the finding that the unexpected activity of the presently claimed compounds is specifically related to fluorine substituted in the 3-position of the pyridine ring; fluorine substitution in other positions on the pyridine ring, e.g., the 5-position, does not cause unusually beneficial activity to result. With the compounds of this invention, it is possible to employ lower dosage rates and still obtain effective control, thus reducing plant residues and any potential environmental contamination and/or toxicological effect on fish and warm blooded animals. Accordingly, the present invention also encompasses herbicidal compositions containing one or more of these active ingredients as well as preemergent and postemergent methods of controlling undesired plant growth, especially in the presence of valuable crops. Such methods comprise applying a herbicidally-effective amount of one or more of said active ingredients to the locus of the undesired plants, that is, the seeds, foliage, rhizomes, stems and roots or other parts of the growing plants or soil in which the plants are growing or may be found.

DETAILED DESCRIPTION OF THE INVENTION

The term "herbicide" is used herein to mean an active ingredient which controls or adversely modifies the growth of plants because of phytotoxic or other effects substantial enough to seriously retard the growth of the plant or further to damage the plant sufficiently to kill the plant.

By "growth controlling" or "herbicidally-effective" amount is meant an amount of active ingredient which causes a modifying effect and includes deviations from natural development, killing, regulation, desiccation, retardation, and the like.

The term "plants" is meant to include germinant seeds, emerging seedlings, rhizomes, stolons and other underground propagules, and established vegetation.

The active ingredients, i.e., new compounds, of the present invention are readily prepared by processes described in the above cited prior art by choosing the appropriate starting materials. The stereoisomers are readily separated as described in European Patent 0002800 referred to above.

Certain of the pyridine reactants employed to make the novel pyridinyloxyphenoxy compounds of this invention are themselves novel compounds and such reactants may be made as generally described hereafter and as specifically set forth in the following examples or by methods analagous thereto, starting with known compounds.

We have unexpectedly found that the fluorine atom in 3-chloro-2-fluoro-5-(trifluoromethyl)pyridine can be readily replaced with a 2-cyano group by reacting said pyridine compound with an alkali metal cyanide, preferably potassium cyanide, in a polar aprotic solvent, preferably dimethylsulfoxide, at a temperature of 10°–50° C., preferably 20°–30° C. We have further found that the chlorine atom in the resulting product, i.e., 3-chloro-2-cyano-5-(trifluoromethyl)pyridine is readily selectively replaced with fluorine by reaction with, e.g., cesium or potassium fluoride in a polar aprotic solvent, preferably dimethyl sulfoxide, at a temperature of 80°–140° C., preferably 90°–100° C. The cyano group in the resulting 2-cyano-3-fluoro-5-(trifluoromethyl)pyridine can be readily converted, by known procedures, to the corresponding acid or amide, as desired. The resulting acid may be readily converted to the corresponding bromine derivative by the Hunsdiecker reaction, as shown in the following Example 4, or the amide may be converted to the corresponding amine and then hydroxy compound by the Hoffmann hypobromite reaction followed by diazotization and replacement by hydroxide as known in the art. The latter is then treated with $POCl_3$ plus $PCl_5$ as known in the art, to prepare, for example, 2-chloro-3-fluoro-5-(trifluoromethyl)pyridine.

Alternatively, 2,3-difluoro-5-(trifluoromethyl)pyridine may be prepared by contacting 2,3-dichloro-5-(trifluoromethyl)pyridine; 2,3-dichloro-5-(trichloromethyl)pyridine or 3-chloro-2-fluoro-5-(trifluoromethyl)pyridine with a fluorinating agent as described in copending application Ser. No. 401,057 filed July 23, 1982 and the 2,3-difluoro-5-(trifluoromethyl)pyridine may be used directly to make 2-(4-((3-fluoro-5-(trifluoromethyl)-2-pyridinyl)oxy)phenoxy)alkanoic acid and derivatives.

The following examples illustrate the present invention and the manner by which it can be practiced but as such are not to be construed as limitations upon the overall scope of the invention.

Example 1

PREPARATION OF 2-CHLORO-3-CYANO-5-(TRIFLUOROMETHYL)-PYRIDINE

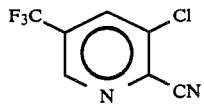

3Chloro-2-fluoro-5-(trifluoromethyl)pyridine (obtained as a by-product from the fluorine exchange reaction when converting 2,3-dichloro-5-trichloromethyl pyridine to 2,3-dichloro-5-(trifluoromethyl)pyridine) (40.0 g, 0.2 mole) was put into 270 ml of dimethyl sulfoxide and stirred while potassium cyanide 14.4 g, 0.221 mole) was spooned in over a 20-minute period. The mixture was then stirred for another 20 minutes. The temperature was held between 23° C. and 28° C. throughout the reaction. The mixture was poured into 600 ml of ice water and the product was extracted into hexane. The hexane was removed on a rotary evaporator. The product was treated with activated charcoal and distilled on a Vigreaux-Claisen still at 108°-110° C. at 30 mm Hg to yield 31.45 g of colorless oil with an analysis of, in percent by weight:

Calculated: C=40.70; H=0.98; N=13.56.
Found: C=40.42; H=0.99; N=13.66.

Example 2

PREPARATION OF 3-FLUORO-2-CYANO-5-(TRIFLUOROMETHYL)-PYRIDINE

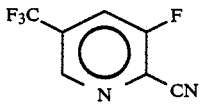

A flask fitted with an air stirrer and a takeoff head was set up. Cesium fluoride (45.6 g, 0.3 mole), potassium carbonate (1.2 g) and 350 ml of dimethyl sulfoxide were put into the flask and heated and stirred under vacuum (30 mm). 120 Ml of dimethyl sulfoxide was distilled off to dry the system. The reaction mixture was cooled to 80° C., the vacuum was released and 3-chloro-2-cyano-5-(trifluoromethyl)pyridine (41.6 g-0.201 mole) was added over a 7-minute period. The reaction mixture was then warmed to 93° C. and held at 93°-111° C. for about 20 minutes. The mixture was then cooled to 54° C., poured over ice and extracted twice with hexane and once with methylene chloride. The solvents were removed and the product was distilled at about 30 mm Hg at 90°-94° C. to yield 29.6 g of colorless oil which had an analysis of, in percent by weight:

Calculated: C=44.22; H=1.06; N=14.74.
Found: C=43.53; H=1.11; N=14.44.

Example 3

PREPARATION OF 3-FLUORO-5-(TRIFLUOROMETHYL)PICOLINIC ACID

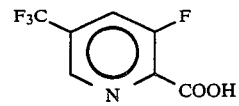

2-Cyano-3-fluoro-5-(trifluoromethyl)-pyridine (11.1 g, 0.0584 mole) was put into 87 ml of 90% sulfuric acid in a beaker. The mixture was stirred and heated at 100°-112° C. for 1-¼ hours. The reaction mixture was then cooled, poured over ice and the solids that came down were filtered off. The solids were dissolved in a dilute solution of NaOH. Any material that didn't go into solution was filtered out and the filtrate was acidified with aqueous HCl and the precipitate was filtered off and dried. This yielded 6.47 g of solid product with an analysis of, in percent by weight:

Calculated: C=40.20; H=1.45; N=6.70.
Found: C=39.29; H=1.35; N=6.98.

1.05 g of a second crop of solids was obtained on standing which exhibited the same IR spectrum as the first solids out. These were combined and used to make the following bromo compound.

Example 4

PREPARATION OF 2-BROMO-3-FLUORO-5-(TRIFLUOROMETHYL)-PYRIDINE

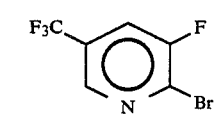

The 3-fluoro-5-(trifluoromethyl)-picolinic acid (7.35 g, 0.035 mole) staring material was put into 150 ml of dry carbon tetrachloride and then red mercuric oxide (9.1 g, 0.042 mole) was added and the mixture was stirred and refluxed 1 hour and 25 minutes. A solution of bromine (6.7 g, 0.042 mole) in 20 ml of dry carbon tetrachloride was added slowly with the mixture at reflux over the next 2-⅓ hours. Light from a UV lamp was directed on the reaction mixture during the addition and the reaction mixture was refluxed for another hour. 25 Ml more of dry carbon tetrachloride was added and the refluxing was continued for about 16 hours more while UV radiation was applied. The reaction was then filtered through CELITE diatomaceous earth to remove the mercury salt. The carbon tetrachloride was removed on a still and the product was distilled over to yield 2.45 g of a yellow oil with analysis of, in percent by weight:

Calculated: C=29.53; H=0.83; N=5.74.
Found: C=29.36; H=0.77; N=5.82.

The gas chromatograph showed the oil to be a 99+% pure compound.

Example 5

PREPARATION OF 2-(4-((3-FLUORO-5-(TRIFLUOROMETHYL)-2-PYRIDINYL)OXY)PHENOXY)PROPANOIC ACID

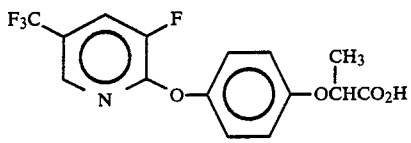

2-(4-Hydroxyphenoxy) propanoic acid (1.80 g, 0.00988 mole) was dissolved in 15 ml of dimethyl sulfoxide. A solution of sodium hydroxide (0.8 g, 0.02 mole in 1 ml of water) was added and the reaction mixture was heated under nitrogen to 48° C. over a 27 minute period. 2-Bromo-3-fluoro-5-(trifluoromethyl)pyridine (2.40 g, 0.00984 mole) dissolved in 5 ml of dimethyl sulfoxide was added and the reaction mixture was heated at 75°-78° C. for 40 minutes. The mixture was poured into 150 ml of cold water and acidified with aqueous HCl. A gum came down. Upon work-up and purification, a fraction (0.45 g) was obtained which had an elemental analysis of, in percent by weight:

Calculated: C=52.18; H=3.21; H=4.06.
Found: C=51.89; H=3.19; N=4.02.

This material had a melting point of 130°-132° C.

Example 6

PREPARATION OF 2-(4-((3-FLUORO-5-TRIFLUOROMETHYL)-2-PYRIDINYL)OXY)PHENOXY)-PROPIONAMIDE

A. A fresh sample of 2-(4-((3-fluoro-5-(trifluoromethyl)-2-pyridinyl)oxy)phenoxy propanoic acid was prepared by the reaction of 2,3-difluoro-5-(trifluoromethyl)pyridine with 2-(4-hydroxyphenoxy)propanoic acid in the presence of 2 moles of sodium hydroxide as above described and 9.0 g (0.026 mole) was refluxed in excess SOCl$_2$ for about ½ hour to prepare the corresponding acid chloride. The excess SOCl$_2$ was removed by heating to 115° C. under an aspirator vacuum. The resulting acid chloride was added to a mixture of concentrated ammonium hydroxide (30 ml) and methanol (60 ml). The flask was rinsed with an additional 15 ml ammonium hydroxide mixed with about 25 ml of methanol and the two fractions were combined. The acid amide formed as a solid which was filtered out, rinsed with water, slurried in water, filtered, dried and analyzed. M.P. 140°-141° C.

| Analysis: | % C | % H | % N |
|---|---|---|---|
| Calculated: | 52.33 | 3.51 | 8.14 |
| Found: | 52.54 | 3.46 | 8.09 |

B. Other propionamides of the invention, as set forth below, were prepared using similar procedures:

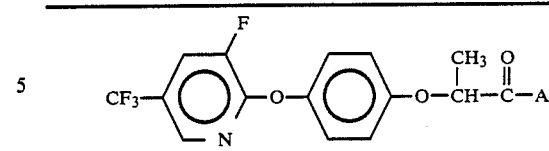

| A | M. P. °C. | Analysis | % C | % H | % N | % Cl |
|---|---|---|---|---|---|---|
| H Cl —N | 142–143.5 | Calc.: | 55.45 | 3.32 | 6.16 | 7.80 |
| | | Found: | 55.88 | 3.34 | 6.11 | 7.70 |

Example 7

PREPARATION OF 2-(4-((3-FLUORO-5-(TRIFLUOROMETHYL)-2-PYRIDINYL)OXY)PHENOXY)-PROPIONITRILE

A portion of the amide prepared in Example 6A (5.68 g, 0.0165 mole) was refluxed with an excess of POCl$_3$ for about 2 hours after which the excess POCl$_3$ was removed by distillation under an aspirator vacuum. The reaction mixture was poured over ice and extracted with methylene chloride. The methylene chloride was removed on a rotary evaporator and the crude material was taken up in hexane and decolorized with charcoal. A gummy material formed which was again placed on the evaporator leaving an oil which was recovered and analyzed.

| Analysis: | % C | % H | % N |
|---|---|---|---|
| Calculated: | 55.22 | 3.09 | 8.59 |
| Found: | 55.64 | 3.00 | 8.81 |

Refractive Index=1.5067 at 25° C.

Example 8

PREPARATION OF 2-(4-((3-FLUORO-5-(TRIFLUOROMETHYL)-2-PYRIDINYL)OXY)PHENOXY)-METHYL PROPANOATE

Following the procedure of Example 6A the acid chloride was prepared by refluxing a portion of the acid from Example 6A with thionyl chloride. The resulting acid chloride (3.45 g, 0.01 mole) was then reacted with methanol (1.0 g, 0.0312 mole) in the presence of triethylamine (2.0 g, 0.02 mole) in 20 ml of toluene at 80°-88° C. The salt was removed by filtration, then rinsed with hexane, the filtrate combined and solvent removed by evaporation. The crude produce was taken up in hexane, some solids removed by filtration and the solution decolorized with charcoal after which solvents were removed under vacuum. The product gradually solidified and was recovered and analyzed. M.P. 50°-52° C.

| Analysis: | % C | % H | % N |
|---|---|---|---|
| Calculated | 53.49 | 3.63 | 3.90 |
| Found: | 53.82 | 3.68 | 3.87 |

Following the above procedure except to employ other alcohols or thioalcohols as the esterifying agent the following compounds were prepared having the general formula:

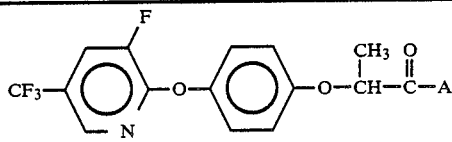

| A | Prep. Properties | | Percentage Compositions | | | |
|---|---|---|---|---|---|---|
| | | | C | H | N | S |
| —OC$_4$H$_9$ | Oil | Calc. | 56.86 | 4.77 | 3.49 | |
| | | Found | 56.85 | 4.77 | 3.51 | |
| —OCH$_2$CH$_2$OCH$_2$CH$_3$ | Oil, R.I. = 1.4944 @ 25° C. | Calc. | 54.68 | 4.59 | 3.36 | |
| | | Found | 54.74 | 4.44 | 3.42 | |
| —SC$_4$H$_9$ | Oil, R.I. = 1.5164 @ 25° C. | Calc. | 54.67 | 4.59 | 3.36 | 7.68 |
| | | Found | 54.87 | 4.54 | 3.39 | 7.59 |

R.I. = refractive index corrected to 25° C.

Example 9

PREPARATION OF 2-(4-((3-FLUORO-5-(TRIFLUOROMETHYL)-2-PYRIDINYL)OXY)PHENOXY-1-PROPANOL

The methyl ester of Example 8 (5.7 g, 0.0159 mole) was dissolved in methanol (75 ml) and a solution of sodium borohydride (3.5 g, 0.0954 mole) was added dropwise to the cooled (19° C.) solution, maintaining the temperature at about 25° C. The mixture was stirred for about 1½ hours after which the temperature was down to 18° C. On standing 30 minutes, the temperature increased to 23.5° C. after which the reaction mixture was warmed to 42° C. (30 minutes), continued stirring without heat for 30 minutes, poured into a beaker and added ice water (200 ml). Extracted with hexane and then twice with methylene chloride. Combined extracts, removed solvents and obtained 4.95 g of the above indicated product as a light yellow oil. R.I.=1.5144 @ 25° C.

| Analysis: | % C | % H | % N |
|---|---|---|---|
| Calculated: | 54.38 | 3.96 | 4.23 |
| Found: | 54.25 | 3.98 | 4.44 |

Example 10

PREPARATION OF THE R-ENANTIOMER OF 2-(4-((3-FLUORO-5-(TRIFLUOROMETHYL)-2-PYRIDINYL)OXY)PHENOXY)PROPIONIC ACID-, METHYL ESTER

A mixture of 2.11 g (7.72 mmol) of 4-(3-fluoro-5-(trifluoromethyl))-2-pyridyloxyphenol (prepared as in Example 12) 1.07 g (7.72 mmol) of anhydrous K$_2$CO$_3$ and 14.1 g (77.2 mmol) of the methane sulfonate of the methyl ester of L-(+)-lactic acid in 16 ml of dry dimethylsulfoxide (DMSO) was stirred at room temperature for 43 hours. The reaction mixture was partitioned between diethylether and water. The organic phase was separated, dried (Na$_2$SO$_4$) and evaporated at reduced pressure to give a colorless liquid. Purification by high pressure liquid chromatography on silica gel eluting with ethyl acetate-hexane (3:22, v/v) gave 2.15 g (78%) of the R-enantiomer of the desired product as a colorless oil: $[\alpha]_D^{25} + 31.4°$ C (CHCl$_3$, C 0.0110 g/ml); IR (CCl$_4$) 1766 and 1741 mcm$^{-1}$; $^1$H NMR (CDCL$_3$) δ 8.0–8.2 (1H, m), 7.5–7.8 (1H, m), 6.7–7.2 (4H, m), 4.71 (1H, q), 3.73 (3H, s) and 1.59 (3H, d); $^{19}$F NMR (CDCl$_3$, ppm upfield from C$_6$F$_6$) 102.1 (s) and 26.3 (d) Anal. Calculated for C$_{16}$H$_{13}$F$_4$NO$_4$: C, 53.49; H, 3.65; N, 3.90.

Found: C, 53.61; H, 3.53; N, 3.86. The optical purity of the sample was determined to be ≧ 90% ee by $^1$H NMR analysis in the presence of Eu(tfc)$_3$.

Example 11

PREPARATION OF THE R-ENANTIOMER OF 2-(4-((3-FLUORO-5-CHLORO-2-PYRIDINYL)OXY)PHENOXY)PROPIONIC ACID-, METHYL ESTER

A mixture of 1.80 g (7.50 mmol) of 4-(3-fluoro-5-chloro)-2-pyridyloxyphenol, 1.04 g (7.50 mmol) of anhydrous K$_2$CO$_3$ and 13.7 g (75.0 mmol) of the methane sulfonate of the methyl ester of L-(+)-lactic acid in 16 ml of dry DMSO was stirred at room temperature for 42 hours. The reaction mixture was partitioned between diethylether and water. The organic phase was separated, dried (Na$_2$SO$_4$) and evaporated at reduced pressure to give a colorless liquid. Purification by high pressure liquid chromatography on silica gel eluting with ethyl acetate-hexane (1:9 v/v) gave 1.82 g (75%) of the R-enantiomer of the desired product as a colorless oil: $[\alpha]_D^{25} + 34.4°$ C. (CHCl$_3$, 0.0112 g/ml); IR (CCl$_4$) 1762 and 1740 cm$^{-1}$; $^1$H NMR (CDCl$_3$) δ 7.82 (1H, d), 7.43 (1H, d of d), 6.7–7.3 (4H, m), 4.69 (1H, q), 3.72 (3H, s) and 1.58 (3H, d); $^{19}$F NMR (CDCl$_3$, ppm upfield from C$_6$F$_6$) 27.2 (d). Analysis: Calculated for C$_{15}$H$_{13}$ClFNO$_4$: C, 55.31; H, 4.02; N, 4.30. Found: C, 55.04; H, 3.85; N, 4.24. The optical purity of the sample was determined to be ≧ 76% ee by $^1$H NMR analysis in the presence of Eu(tfc)$_3$.

Example 12

PREPARATION OF 4-((3-FLUORO-5-(TRIFLUOROMETHYL)-2-PYRIDINYL)OXY)PHENOL

Hydroquinone (4.4 g, 0.04 mole) was dissolved in 65 ml of dimethylsulfoxide and powdered sodium hydroxide (1.4 g, 0.035 mole) was added in one portion and the mixture stirred under nitrogen atmosphere for 10 minutes to convert to the sodium salt. 2,3-Difluoro-5-(trifluoromethyl)pyridine (6.0 g, 0.033 mole) was then added and the mixture was stirred at 50° C. for 1.5 hours then warmed to 60° C. for a moment, let cool for 15 minutes and then poured into 500 ml of cold water. Additional sodium hydroxide (~3 g in water) was added to convert the desired product to its sodium salt. The insoluble bis-derivative was then removed by extraction with hexane. The clear aqueous phase was separated, cooled and acidified with concentrated hydrochloric acid. The solid which separated was collected on a filter, washed, dried on a vacuum funnel and taken up in hot hexane. After treating with decolorizing carbon, filtering, concentrating and cooling the white crystalline product separated. Yield: 2.6 g. M.P. 97.5–98.5.

| Analysis: | % C | % H | % N |
|---|---|---|---|
| Calculated: | 52.76 | 2.58 | 5.12 |
| Found: | 52.71 | 2.57 | 5.12 |

Example 13

PREPARATION OF 5-CHLORO-2,3-DIFLUOROPYRIDINE

Cesium fluoride (125 g, 0.82 mol) and DMSO (300 ml) were placed in a fluorination flask equipped with a mechanical stirrer, a thermometer, and a distilling head. About 50 ml DMSO were distilled off, under vacuum, to dry the system. 2,3,5-Trichloropyridine (50 g, 0.27 mol) and potassium carbonate (2.5 g, 0.018 mol) were added and the mixture was heated at 130°–140° C. for 7 hours, with vigorous stirring. The product was distilled directly out of the reaction mixture, under vacuum. The DMSO was watered out and the product was redistilled to give a clear, colorless liquid (11.9 g, 29% of theoretical, b.p. 70°–73° C. @ 85 mmHg).

| Analysis: | % C | % H | % N | % Cl |
|---|---|---|---|---|
| Calculated: | 40.16 | 1.35 | 9.37 | 23.71 |
| Found: | 39.54 | 1.36 | 9.44 | 23.92 |

Example 14

PREPARATION OF 5-BROMO-2,3-DIFLUOROPYRIDINE

Cesium fluoride (28.8 g, 0.19 mol), potassium carbonate (1.0 g, 0.007 mol) and sulfolane (190 ml) were placed in a fluorination flask equipped with a mechanical stirrer, a thermometer, and a distilling head. About 20 ml of sulfolane were distilled off, under vacuum, to dry the system. 2,3,5-Tribromopyridine (20 g, 0.063 mol) was added and the mixture was heated at 180° C. for 2½ days. The product was distilled directly out of the reaction mixture to yield a clear, colorless liquid (3.94 g, 32%) that was 80% 5-bromo-2,3-difluoropyridine and 20% 3-bromo2,5-difluoropyridine isomer.

| Analysis: | % C | % H | % N |
|---|---|---|---|
| Calculated: | 30.95 | 1.04 | 7.2 |
| Found: | 31.36 | 1.14 | 7.32 |

Example 15

PREPARATION OF 4-(5-CHLORO-3-FLUORO-2-PYRIDINYLOXY)-PHENOL

A solution of NaOH (1.76 g, 0.044 mol) in a few ml of water was added to hydroquinine (4.86 g, 0.040 mol) in 250 ml DMSO. The mixture was stirred under nitrogen for 20 minutes. 5-Chloro-2,3-difluoropyridine (6.0 g, 0.040 mol) was added. The reaction mixture was heated at 60°–70° C. for 3 hours, then poured over ice. Aqueous NaOh was added to pH 12 and the solid diether side-product was filtered off. The filtrate was acidified, extracted with ether, treated with Norite adsorbent, and the solvent was removed by rotary evaporation to give a yellow oil which solidified on standing and was purified by high pressure liquid chromatography (HPLC) (80% hexane/20% ethyl acetate) to give a white solid (2.5 g, 26% yield, m.p. 90°–92° C.).

| Analysis: | % C | % H | % N |
|---|---|---|---|
| Calculated: | 55.14 | 2.94 | 5.85 |
| Found: | 55.05 | 2.93 | 5.65 |

Example 16

PREPARATION OF 2-(4-(3-FLUORO-5-CHLORO-2-PYRIDINYLOXY)-PHENOXY)PROPIONIC ACID METHYL ESTER

A solution of NaOH (2.7 g, 0.068 mol) in a few ml of water was added to 2-(4-hydroxyphenoxy)propionic acid (6.09 g, 0.033 mol) in 55 ml DMSO and the mixture was stirred for 20 minutes under nitrogen. 5-Chloro-2,3-difluoropyridine (5.0 g, 0.033 mol) was added and the mixture was heated at 70° C. for 5 hours. The reaction was then poured over ice and extracted with $CH_2Cl_2$. The organic layer was washed with water, dried over $Na_2SO_4$ and the solvent removed by rotary evaporation. The residual oil was dissolved in 130 ml dry methanol, p-toluene sulfonic acid (0.5 g, 0.003 mmol) was added and the mixture was stirred at room temperature for 24 hours. The methanol was removed by rotary evaporation. The residue was taken up in ether, washed with dilute aqueous NaOH, and dried over $Na_2SO_4$. The ether was removed by rotary evaporation to yield a tan oil which solidified on trituration with methylcyclohexane to give a white solid (6.4 g, 59%, m.p. 53°–56° C.).

| Analysis: | % C | % H | % N |
|---|---|---|---|
| Calculated: | 55.31 | 4.02 | 4.30 |
| Found: | 54.91 | 4.05 | 4.21 |

Example 17

PREPARATION OF 2-(4-(5-BROMO-3-FLUORO-2-PYRIDINYLOXY)-PHENOXY)PROPIONIC ACID

A solution of NaOH (0.54 g, 0.013 mol) in a few ml of water was added to -2-(4-hydroxyphenoxy)propionic acid (1.22 g, 0.0067 mol) in 20 ml DMSO and the mixture was stirred for 20 minutes under $N_2$. 5-Bromo-2,3-difluoropyridine (1.3 g, 0.0067 mol) was added and the mixture was stirred for 5½ hours at 80°–90° C. The reaction mixture was poured into water, acidified with concentrated HCl to pH 1 and extracted into $CH_2Cl_2$. The solution was dried over $Na_2SO_4$ and the solvent was removed by rotary evaporation to yield a gum which became an off-white solid (0.78 g, 33%, M.P.94°–97° C.) upon standing.

| Analysis: | % C | % H | % N | % Br |
|---|---|---|---|---|
| Calculated: | 47.21 | 3.11 | 3.93 | 22.43 |
| Found: | 46.88 | 3.12 | 3.94 | 22.34 |

The compounds of the present invention have been found to be suitable for use in methods for the selective pre- and postemergent control of annual and perennial grassy weeds. These compounds, the active ingredients of the present invention, have been found to have advantage over prior art compounds in the control of annual and perennial grassy weeds in that the present compounds control such weeds at substantially lower dosage rates. In addition, the present compounds are sufficiently tolerant towards most broad leafed crops to contemplate control of grassy weeds therein at substantially commercially practicable levels, particularly so with the preferred compounds. In addition, certain of the compounds have sufficient tolerance towards cereal crops such as wheat to enable selective grassy weed control in these crops as well.

For such uses, unmodified active ingredients of the present invention can be employed. However, the present invention embraces the use of the compounds in composition form with an inert material, known in the art as an agricultural adjuvant or carrier, in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The herbicidally effective concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 parts of the additional compound(s).

The active ingredients of the present invention have been found to possess desirable herbicidal activity in general against grassy weeds such as foxtail, barnyardgrass, wild oats, seedling johnsongrass and crabgrass in preemergent operations and also against the same grasses in postemergent operations while being tolerant to important broadleaf crops such as cotton, soybeans, sugarbeets and rape and in the case of certain of the compounds, certain cereal crops such as wheat. These compounds are also uniquely effective in selectively controlling perennial grassy weeds such as johnsongrass, quackgrass, bermudagrass and dallisgrass.

The active ingredients of the present invention have been found to possess particularly desirable herbicidal activity against wild oats, foxtail, barnyardgrass, crabgrass and seedling johnsongrass in postemergent operations as well as desirable broad spectrum activity against the perennial grassy weeds listed above and at lower dosage rates than the substituted propanoates and propanols of the prior art while showing high selectivity to broadleaf crops and, in the case of certain of the compounds, wheat.

The present compounds which are substituted propanols or propyl ethers are more effective in preemergent operations than in postemergent applications.

The exact rate to be applied is dependent not only on a specific active ingredient being applied, but also on a particular action desired, the plant species to be modified and the stage of growth thereof as well as the part of the plant to be contacted with the toxic active ingredient. Thus, all of the active ingredients of the present invention and compositions containing the same may not be equally effective at similar concentrations or against the same plant species.

In postemergent operations a dosage of about 0.05 to about 20 pounds/acre (0.056–22.4 kg/hectare) is generally applicable, although not all compounds are equally effective and some weeds are more difficult to control. Thus, a dosage rate in the range of about 0.01 to about 1.0 pound/acre (0.01–1.12 kg/hectare) is preferred in postemergent control of annual grassy weeks, while about 0.05 to about 5 pounds/acre (0.056–5.6 kg/hectare) is preferred dosage range for the postemergent control of perennial grassy weeds. In applications to tolerant crops a weed controlling but less than crop damaging amount of from about 0.005 to about 1.0 lb/acre (0.0056 to 1.12 kgs/hectare) is generally employed.

In preemergent operations a dosage rate of 0.01 to 10 lbs/acre (0.011 to 11.2 kgs/hectare), preferably 0.05 to 2.0 lbs/acre (0.056 to 2.25 kgs/hectare) and most preferably 0.1 to 1 lb/acre (0.11 to 1.12 kgs/hectare) is generally employed.

The following examples illustrate effects of the compounds of this invention.

Example 18

In representative operations, each compound to be utilized in a series of tests is dissolved in acetone to one-half of the final volume (twice the final concentration) to be used and the acetone solution in each case is admixed with an equal volume of water containing 0.1 percent by weight of the non-ionic surfactant TWEEN ® 20 (a polyoxyethylene sorbitan monolaurate). The compositions, generally in the nature of an emulsion, were employed to spray separate respective plant species which had been grown to a height of 2–6 inches in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other portions of the plants were left untreated to serve as controls. After treatment, the plants were maintained for about two weeks under greenhouse conditions conducive for good plant growth and watered as necessary. The specific plant species, test compound and dosage and the percent postemergent control obtained are set forth in the table below. Control refers to the reduction in growth compared to the observed results of the same untreated species. Note the "NT" means "not tested".

Plant species in these tests were the following:

| Common Name | Scientific Name |
|---|---|
| Barnyardgrass (Watergrass) | *Echinochloa crusgalli* |
| Crabgrass | *Digitaria sanquinalis* |
| Yellow foxtail | *Setaria lutescens* |
| Johnson grass | *Sorghum halepense* |
| Wild Oats | *Avena fatua* |
| Cotton | *Gossypium hirsutum* |
| Rape | *Brassica napus* |
| Soybeans | *Glycine max* |
| Sugarbeet | *Beta vulgaris* |
| Wheat | *Triticum aestivum* |

POSTEMERGENT CONTROL OF PLANT SPECIES

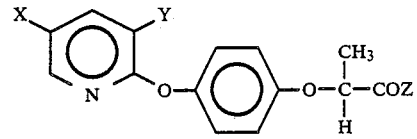

| Compound Tested | | | | Dosage in ppm | | | | | |
|---|---|---|---|---|---|---|---|---|---|
| X | Y | Z | Plant Species | 125 | 62.5 | 31.25 | 15.6 | 7.8 | 3.9 |
| CF3 | F | OH | Cotton | 0 | 0 | 0 | 0 | 0 | 0 |
| | | | Rape | 0 | 0 | 0 | 0 | 0 | 0 |
| | | | Soybean | 0 | 0 | 0 | 0 | 0 | 0 |
| | | | Sugarbeet | 0 | 0 | 0 | 0 | 0 | 0 |
| | | | Barnyardgrass | 100 | 100 | 100 | 80 | 30 | 0 |
| | | | Crabgrass | 100 | 100 | 100 | 90 | 80 | 15 |
| | | | Yellow Foxtail | 100 | 100 | 100 | 65 | 20 | 0 |
| | | | Johnson grass | 100 | 100 | 100 | 100 | 50 | 0 |
| | | | Wild Oats | 100 | 100 | 80 | 40 | 0 | 0 |
| | | | Wheat | 100 | 100 | 90 | 40 | 0 | NT |
| Cl | F | OCH3 | Cotton | 0 | 0 | 0 | 0 | 0 | 0 |
| | | | Rape | 0 | 0 | 0 | 0 | 0 | 0 |
| | | | Soybean | 0 | 0 | 0 | 0 | 0 | 0 |
| | | | Sugarbeet | 0 | 0 | 0 | 0 | 0 | 0 |
| | | | Barnyardgrass | 100 | 100 | 100 | 95 | 10 | 0 |
| | | | Crabgrass | 100 | 100 | 100 | 100 | 100 | 60 |
| | | | Yellow Foxtail | 100 | 100 | 100 | 90 | 0 | NT |
| | | | Johnson grass | 100 | 100 | 100 | 100 | 100 | 20 |
| | | | Wild Oats | 100 | 100 | 20 | 0 | 0 | NT |
| | | | Wheat | 30 | 0 | 0 | 0 | 0 | NT |
| Br | F | OH | Cotton | 0 | 0 | 0 | 0 | 0 | 0 |
| | | | Rape | 0 | 0 | 0 | 0 | 0 | 0 |
| | | | Soybean | 0 | 0 | 0 | 0 | 0 | 0 |
| | | | Sugarbeets | 0 | 0 | 0 | 0 | 0 | 0 |
| | | | Barnyardgrass | 100 | 100 | 100 | 100 | 10 | 0 |
| | | | Crabgrass | 100 | 100 | 100 | 100 | 100 | 0 |
| | | | Yellow Foxtail | 100 | 100 | 100 | 100 | 100 | 0 |
| | | | Johnson grass | 100 | 100 | 100 | 100 | 70 | 0 |
| | | | Wild Oats | 100 | 100 | 100 | 0 | 0 | 0 |
| | | | Wheat | 100 | 90 | 70 | 20 | 0 | NT |
| CF3 | F | OCH3 (R enantiomer - 90% optical purity) | Cotton | 0 | 0 | 0 | 0 | 0 | 0 |
| | | | Rape | 0 | 0 | 0 | 0 | 0 | 0 |
| | | | Soybean | 0 | 0 | 0 | 0 | 0 | 0 |
| | | | Sugarbeets | 0 | 0 | 0 | 0 | 0 | 0 |
| | | | Barnyardgrass | 100 | 100 | 100 | 100 | 95 | 10 |
| | | | Crabgrass | 100 | 100 | 100 | 100 | 100 | 90 |
| | | | Yellow Foxtail | 100 | 100 | 95 | 90 | 40 | 0 |
| | | | Johnson grass | 100 | 100 | 100 | 100 | 70 | 70 |
| | | | Wild Oats | 100 | 100 | 100 | 100 | 0 | 0 |
| | | | Wheat | 90 | 100 | 100 | 55 | 65 | 0 |
| CH3 | F | OCH3 | Cotton | 0 | 0 | 0 | 0 | 0 | 0 |
| | | | Rape | 0 | 0 | 0 | 0 | 0 | 0 |
| | | | Soybean | 0 | 0 | 0 | 0 | 0 | 0 |
| | | | Sugarbeets | 0 | 0 | 0 | 0 | 0 | 0 |
| | | | Barnyardgrass | 100 | 100 | 100 | 100 | 10 | 0 |
| | | | Crabgrass | 100 | 100 | 100 | 100 | 90 | 50 |
| | | | Yellow Foxtail | 100 | 100 | 40 | 50 | 10 | 0 |
| | | | Johnson grass | 100 | 100 | 100 | 90 | 90 | 50 |
| | | | Wild Oats | 100 | 100 | 90 | 20 | 0 | 0 |
| | | | Wheat | 100 | 100 | 20 | 0 | NT | NT |
| CF3 | F | OC2H4OC2H5 | Cotton | 0 | 0 | 0 | 0 | 0 | 0 |
| | | | Rape | 0 | 0 | 0 | 0 | 0 | 0 |
| | | | Soybean | 0 | 0 | 0 | 0 | 0 | 0 |

-continued
POSTEMERGENT CONTROL OF PLANT SPECIES

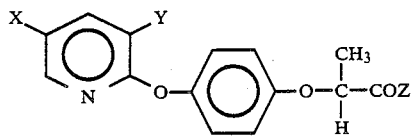

| Compound Tested | | | | Dosage in ppm | | | | | |
|---|---|---|---|---|---|---|---|---|---|
| X | Y | Z | Plant Species | 125 | 62.5 | 31.25 | 15.6 | 7.8 | 3.9 |
| | | | Sugarbeets | 0 | 0 | 0 | 0 | 0 | 0 |
| | | | Barnyardgrass | 100 | 100 | 100 | 100 | 90 | 70 |
| | | | Crabgrass | 100 | 100 | 100 | 100 | 100 | 90 |
| | | | Yellow Foxtail | 100 | 100 | 100 | 100 | 85 | 10 |
| | | | Johnson grass | 100 | 100 | 100 | 100 | 100 | 90 |
| | | | Wild Oats | 100 | 100 | 90 | 80 | 40 | 0 |
| | | | Wheat | 100 | 100 | 90 | 85 | 40 | 0 |
| CF$_3$ | F | N—H / Cl | Cotton | 0 | 0 | 0 | 0 | 0 | 0 |
| | | | Rape | 0 | 0 | 0 | 0 | 0 | 0 |
| | | | Soybean | 0 | 0 | 0 | 0 | 0 | 0 |
| | | | Sugarbeets | 0 | 0 | 0 | 0 | 0 | 0 |
| | | | Barnyardgrass | 100 | 100 | 90 | 70 | 20 | 0 |
| | | | Crabgrass | 100 | 100 | 100 | 100 | 90 | 40 |
| | | | Yellow Foxtail | 100 | 100 | 100 | 100 | 80 | 10 |
| | | | Johnson grass | 100 | 100 | 100 | 100 | 95 | 80 |
| | | | Wild Oats | 100 | 100 | 30 | 50 | 20 | 0 |
| | | | Wheat | 100 | 100 | 80 | 40 | 10 | 0 |
| CF$_3$ | F | SC$_4$H$_9$ | Cotton | 0 | 0 | 0 | 0 | 0 | 0 |
| | | | Rape | 0 | 0 | 0 | 0 | 0 | 0 |
| | | | Soybean | 0 | 0 | 0 | 0 | 0 | 0 |
| | | | Sugarbeets | 0 | 0 | 0 | 0 | 0 | 0 |
| | | | Barnyardgrass | 100 | 100 | 100 | 70 | 80 | 40 |
| | | | Crabgrass | 100 | 100 | 100 | 100 | 100 | 90 |
| | | | Yellow Foxtail | 100 | 100 | 100 | 100 | 95 | 65 |
| | | | Johnson grass | 100 | 100 | 100 | 95 | 100 | 75 |
| | | | Wild Oats | 100 | 100 | 90 | 10 | 0 | NT |
| | | | Wheat | 100 | 100 | 90 | 80 | 10 | 0 |
| CF$_3$ | F | NH$_2$ | Cotton | 0 | 0 | 0 | 0 | 0 | 0 |
| | | | Rape | 0 | 0 | 0 | 0 | 0 | 0 |
| | | | Soybean | 0 | 0 | 0 | 0 | 0 | 0 |
| | | | Sugarbeets | 0 | 0 | 0 | 0 | 0 | 0 |
| | | | Barnyardgrass | 100 | 100 | 100 | 95 | 95 | 20 |
| | | | Crabgrass | 100 | 100 | 100 | 100 | 100 | 90 |
| | | | Yellow Foxtail | 100 | 100 | 100 | 100 | 90 | 15 |
| | | | Johnson grass | 100 | 100 | 100 | 100 | 95 | 90 |
| | | | Wild Oats | 100 | 100 | 90 | 80 | 70 | 0 |
| | | | Wheat | 100 | 100 | 90 | 80 | 75 | 50 |
| Cl | F | OCH$_3$ (R enantiomer - ≧75% optical purity) | Sugarbeets | NT | 0 | 0 | 0 | 0 | 0 |
| | | | Barnyardgrass | NT | 100 | 100 | 100 | 100 | 25 |
| | | | Crabgrass | NT | 100 | 100 | 100 | 100 | 100 |
| | | | Yellow Foxtail | NT | 100 | 100 | 100 | 100 | 50 |
| | | | Johnson grass | NT | 100 | 100 | 100 | 90 | 10 |
| | | | Wild Oats | NT | 100 | 80 | 70 | 70 | 0 |
| | | | Wheat | NT | 75 | 20 | 0 | 0 | 0 |

Example 19

So as to clearly illustrate the phytotoxic properties of the various active ingredients of the present invention applied premergently, a controlled greenhouse experiment is described below.

The seeds of various species of plants were planted in beds of good agricultural soil in a greenhouse. A number of compositions of the present invention, generally in the nature of an aqueous emulsion, were applied at rates listed in the table so as to deposit a predetermined amount of active ingredients uniformly throughout the surface of the bed. Another seed bed was treated only with water to serve as a control. After treatment the seed beds were maintained for two weeks under greenhouse conditions conducive for good plant growth and watered as necessary. The specific plant species, test compound, and dosage and the percent preemergent control are set forth in the table below. Control refers to the reduction in growth compared to the observed results of the same untreated species.

PREEMERGENT CONTROL OF PLANT SPECIES

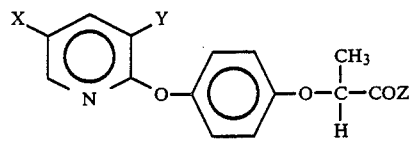

| Compound Tested | | | | Dosage (Lb/Acre) | | | | |
|---|---|---|---|---|---|---|---|---|
| X | Y | Z | Plant Species | .25 | .125 | .063 | .031 | .016 |
| $CF_3$ | F | OH | Cotton | 0 | 0 | 0 | 0 | 0 |
| | | | Rape | 0 | 0 | 0 | 0 | 0 |
| | | | Soybean | 0 | 0 | 0 | 0 | 0 |
| | | | Sugarbeet | 0 | 0 | 0 | 0 | 0 |
| | | | Barnyardgrass | 100 | 100 | 97 | 85 | 10 |
| | | | Crabgrass | 100 | 100 | 100 | 60 | 5 |
| | | | Yellow Foxtail | 100 | 100 | 85 | 30 | 10 |
| | | | Johnson grass | 100 | 98 | 97 | 65 | 25 |
| | | | Wild Oats | 100 | 99 | 80 | 65 | 10 |
| | | | Wheat | 100 | 97 | 40 | 20 | 0 |
| $CF_3$ | F | $OCH_3$ | Cotton | 0 | 0 | 0 | 0 | 0 |
| (R enantiomer - | | | Rape | 0 | 0 | 0 | 0 | 0 |
| $\geq$90% optical | | | Soybean | 0 | 0 | 0 | 0 | 0 |
| purity) | | | Sugarbeet | 0 | 0 | 0 | 0 | 0 |
| | | | Barnyardgrass | 100 | 100 | 100 | 95 | 50 |
| | | | Crabgrass | 100 | 100 | 100 | 100 | 100 |
| | | | Yellow Foxtail | 100 | 100 | 100 | 90 | 70 |
| | | | Johnson grass | 100 | 100 | 100 | 100 | 90 |
| | | | Wild Oats | 100 | 100 | 98 | 40 | 30 |
| | | | Wheat | 100 | 100 | 100 | 90 | 40 |
| $CF_3$ | F | $OCH_3$ | Barnyardgrass | 100 | 100 | 80 | 30 | 10 |
| | | | Crabgrass | 100 | 100 | 100 | 100 | 90 |
| | | | Yellow Foxtail | 100 | 100 | 50 | 40 | 10 |
| | | | Johnson grass | 100 | 100 | 100 | 90 | 50 |
| | | | Wild Oats | 100 | 100 | 95 | 30 | 0 |
| | | | Wheat | 100 | 100 | 98 | 40 | 10 |
| | | | At 0.25 lb/acre there was no damage to cotton, rape, soybeans or sugarbeets | | | | | |
| $CF_3$ | F | $OC_4H_9$ | Barnyardgrass | NT | 100 | 90 | 50 | 0 |
| | | | Crabgrass | NT | 100 | 100 | 100 | 40 |
| | | | Yellow Foxtail | NT | 100 | 100 | 30 | 0 |
| | | | Johnson grass | NT | 100 | 100 | 100 | 20 |
| | | | Wild Oats | NT | 40 | 30 | 0 | 0 |
| | | | Wheat | NT | 100 | 100 | 60 | 10 |
| | | | At 0.25 lb/acre there was no damage to cotton, rape, soybeans or sugarbeets | | | | | |
| $CF_3$ | F | $NH_2$ | Barnyardgrass | 100 | 100 | 70 | 20 | 0 |
| | | | Crabgrass | 100 | 100 | 100 | 100 | 30 |
| | | | Yellow Foxtail | 100 | 100 | 100 | 30 | 0 |
| | | | Johnson grass | 100 | 100 | 80 | 60 | 10 |
| | | | Wild Oats | 100 | 100 | 100 | 30 | 0 |
| | | | Wheat | 100 | 100 | 97 | 70 | 0 |
| | | | At 0.25 lb/acre there was no damage to cotton, rape, soybeans or sugarbeets | | | | | |
| $CF_3$ | F | H<br>\|<br>N Cl | Barnyardgrass | 100 | 100 | 70 | 20 | 0 |
| | | | Crabgrass | 100 | 100 | 100 | 100 | 40 |
| | | | Yellow Foxtail | 100 | 100 | 100 | 95 | 30 |
| | | | Johnson grass | 100 | 100 | 100 | 30 | 0 |
| | | | Wild Oats | 100 | 100 | 60 | 20 | 0 |
| | | | Wheat | 100 | 50 | 30 | 0 | NT |
| | | | At 0.25 lb/acre there was no damage to cotton, rape, soybeans or sugarbeets | | | | | |
| $CF_3$ | F | $SC_4H_9$ | Barnyardgrass | 100 | 100 | 100 | 30 | 0 |
| | | | Crabgrass | 100 | 100 | 100 | 100 | 100 |
| | | | Yellow Foxtail | 100 | 100 | 100 | 30 | 0 |
| | | | Johnson grass | 100 | 100 | 90 | 80 | 30 |
| | | | Wild Oats | 100 | 100 | 100 | 70 | 30 |
| | | | Wheat | 100 | 100 | 100 | 70 | 20 |
| | | | At 0.25 lb/acre there was no damage to cotton, rape, soybeans or sugarbeets | | | | | |
| $CF_3$ | F | CN* | Barnyardgrass | 100 | 100 | 80 | 50 | 10 |
| *Replaces COZ | | | Crabgrass | 100 | 100 | 100 | 100 | 30 |
| | | | Yellow Foxtail | 100 | 100 | 90 | 90 | 30 |
| | | | Johnson grass | 100 | 100 | 95 | 60 | 20 |
| | | | Wild Oats | NT | 100 | 100 | 20 | 0 |
| | | | Wheat | 100 | 30 | 40 | 0 | 0 |
| | | | At 0.25 lb/acre there was no damage to cotton, rape, soybeans or sugarbeets | | | | | |
| $CF_3$ | F | $OC_2H_4OC_2H_5$ | Barnyardgrass | 100 | 100 | 100 | 20 | 0 |

-continued
PREEMERGENT CONTROL OF PLANT SPECIES

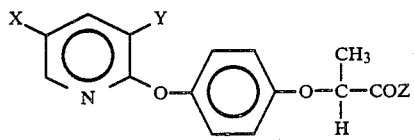

| Compound Tested | | | | Dosage (Lb/Acre) | | | | |
|---|---|---|---|---|---|---|---|---|
| X | Y | Z | Plant Species | .25 | .125 | .063 | .031 | .016 |
| | | | Crabgrass | 100 | 100 | 100 | 50 | 10 |
| | | | Yellow Foxtail | 100 | 100 | 90 | 20 | 0 |
| | | | Johnson grass | 100 | 90 | 80 | 20 | 0 |
| | | | Wild Oats | 100 | 100 | 70 | 30 | 0 |
| | | | Wheat | 100 | 100 | 100 | 50 | 20 |
| | | | At 0.25 lb/acre there was no damage to cotton, rape, soybeans or sugarbeets | | | | | |
| $CF_3$ | F | $CH_2OH$* | Barnyardgrass | 100 | 100 | 100 | 70 | 40 |
| *Replaces Radical | | | Crabgrass | 100 | 100 | 100 | 100 | 100 |
| —COZ | | | Yellow Foxtail | 100 | 100 | 100 | 100 | 50 |
| | | | Johnson grass | 100 | 90 | 80 | 20 | 0 |
| | | | Wild Oats | 100 | 100 | 40 | 10 | 0 |
| | | | Wheat | 100 | 100 | 100 | 50 | 40 |
| | | | At 0.25 lb/acre there was no damage to cotton, rape, soybeans or sugarbeets | | | | | |
| Cl | F | $OCH_3$ | Barnyardgrass | 100 | 100 | 80 | 30 | 10 |
| | | | Crabgrass | 100 | 100 | 100 | 98 | 30 |
| | | | Yellow Foxtail | 100 | 100 | 90 | 30 | 10 |
| | | | Johnson grass | 100 | 80 | 90 | 40 | 20 |
| | | | Wild Oats | 100 | 100 | 98 | 40 | 10 |
| | | | Wheat | 20 | 10 | 0 | 0 | 0 |
| | | | At 0.25 lb/acre there was no damage to cotton, rape, soybeans or sugarbeets | | | | | |
| Br | F | OH | Barnyardgrass | 100 | 100 | 100 | 40 | 10 |
| | | | Crabgrass | 100 | 100 | 100 | 40 | 0 |
| | | | Yellow Foxtail | 70 | 90 | 40 | 10 | 0 |
| | | | Johnson grass | 100 | 100 | 98 | 60 | 10 |
| | | | Wild Oats | 100 | 30 | 10 | 0 | NT |
| | | | Wheat | 100 | 70 | 20 | 0 | NT |
| | | | At 0.25 lb/acre there was no damage to cotton, rape, soybeans or sugarbeets | | | | | |

Other compounds within the scope of the present invention, e.g., the various metal salts, amine salts and other derivatives of the above described compounds may also be employed to control certain plant species with results commensurate to the above described results.

Various modifications may be made in the present invention without departing from the spirit or scope thereof and it is understood that we limit ourselves only as defined in the appended claims.

What is claimed is:

1. A pyridine compound from the group consisting of 5-chloro-2,3-difluoropyridine or 5-bromo-2,3-difluoropyridine.

2. Compound of claim 1 which is 5-chloro-2,3-difluoropyridine.

3. Compound of claim 1 which is 5-bromo-2,3-difluoropyridine.